(12) United States Patent
Bordier et al.

(10) Patent No.: US 7,413,580 B2
(45) Date of Patent: Aug. 19, 2008

(54) DOUBLE PARA-PHENYLENEDIAMINES JOINED BY A LINKER ARM SUBSTITUTED WITH ONE OR MORE CARBOXYLIC RADICALS AND/OR DERIVATIVES AND USE IN DYEING

(75) Inventors: Thierry Bordier, Tremblay en France (FR); Stéphane Sabelle, Paris (FR)

(73) Assignee: L'Oreal S.A., Paris (FR)

( * ) Notice: Subject to any disclaimer, the term of this patent is extended or adjusted under 35 U.S.C. 154(b) by 83 days.

(21) Appl. No.: 11/476,821

(22) Filed: Jun. 29, 2006

(65) Prior Publication Data

US 2007/0011826 A1    Jan. 18, 2007

Related U.S. Application Data

(60) Provisional application No. 60/698,936, filed on Jul. 14, 2005.

(30) Foreign Application Priority Data

Jun. 29, 2005   (FR) ................... 05 51810

(51) Int. Cl.
*A61K 5/10*   (2006.01)
*C07C 211/00*   (2006.01)

(52) U.S. Cl. ............... 8/405; 8/406; 8/407; 8/408; 8/409; 8/410; 8/411; 8/412; 8/414; 8/415; 8/435; 564/441

(58) Field of Classification Search ............. 8/405, 8/406, 407, 408, 409, 410, 411, 412, 414, 8/415, 435; 564/371, 441
See application file for complete search history.

(56) References Cited

U.S. PATENT DOCUMENTS

| | | | |
|---|---|---|---|
| 2,452,535 A | 11/1948 | Johnson et al. | |
| 3,532,743 A | 10/1970 | Kalopissis et al. | |
| 3,694,138 A | 9/1972 | Kalopissis et al. | |
| 4,003,699 A | 1/1977 | Rose et al. | |
| 4,010,200 A | 3/1977 | Kalopissis et al. | |
| RE30,199 E | 1/1980 | Rose et al. | |
| 4,823,985 A | 4/1989 | Grollier et al. | |
| 5,061,289 A | 10/1991 | Clausen et al. | |
| 5,114,429 A | 5/1992 | Junino et al. | |
| 5,380,340 A | 1/1995 | Neunhoeffer et al. | |
| 5,534,036 A * | 7/1996 | Junino et al. ............ | 8/411 |
| 5,534,267 A | 7/1996 | Neunhoeffer et al. | |
| 5,663,366 A | 9/1997 | Neunhoeffer et al. | |
| 5,708,151 A | 1/1998 | Mockli | |
| 5,766,576 A | 6/1998 | Lowe et al. | |
| 5,804,171 A | 9/1998 | Audousset et al. | |
| 5,885,564 A | 3/1999 | Zastro et al. | |
| 6,099,592 A | 8/2000 | Vidal et al. | |
| 6,277,156 B1 | 8/2001 | Audousset | |
| 6,284,003 B1 | 9/2001 | Rose et al. | |
| 6,338,741 B1 | 1/2002 | Vidal et al. | |
| 6,379,398 B1 | 4/2002 | Genet et al. | |
| 6,630,004 B1 | 10/2003 | Philippe et al. | |
| 6,645,258 B2 | 11/2003 | Vidal et al. | |
| 6,699,296 B2 | 3/2004 | Chassot | |
| 6,730,789 B1 | 5/2004 | Birault et al. | |
| 6,923,835 B2 | 8/2005 | Sabelle et al. | |
| 7,303,591 B2 | 12/2007 | Greaves et al. | |
| 2004/0199018 A1 | 10/2004 | Knuebel et al. | |
| 2006/0265818 A1 | 11/2006 | Seiler et al. | |

FOREIGN PATENT DOCUMENTS

| | | |
|---|---|---|
| DE | 23 59 399 | 6/1975 |
| DE | 38 43 892 | 9/1990 |
| DE | 41 33 957 | 4/1993 |
| DE | 195 43 988 | 5/1997 |
| DE | 101 44 226 | 3/2003 |
| EP | 0 714 954 | 6/1996 |
| EP | 0 722 711 | 7/1996 |
| EP | 0 770 375 | 5/1997 |
| EP | 0 872 466 | 10/1998 |
| EP | 0 908 445 | 4/1999 |
| EP | 0 984 006 | 3/2000 |
| EP | 1 396 486 | 3/2004 |
| EP | 1 739 084 | 1/2007 |
| FR | 2 016 123 | 5/1970 |
| FR | 2 586 913 | 3/1987 |
| FR | 2 733 749 | 11/1996 |
| FR | 2 801 308 | 5/2001 |
| GB | 1026978 | 4/1966 |
| GB | 1153196 | 5/1969 |
| JP | 2-019576 | 1/1990 |
| JP | 5-163124 | 6/1993 |
| JP | 8-041329 | 2/1996 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 98/01434 | 1/1998 |
| WO | WO 99/11230 | 3/1999 |
| WO | WO 01/72686 | 10/2001 |
| WO | WO 02/06207 | 1/2002 |
| WO | WO 02/055500 | 7/2002 |
| WO | WO 03/024917 | 3/2003 |
| WO | WO 05/051336 | 6/2005 |

OTHER PUBLICATIONS

STIC Search Report dated Jan. 24, 2008.*

(Continued)

*Primary Examiner*—Eisa B Elhilo
(74) *Attorney, Agent, or Firm*—Finnegan, Henderson, Farabow, Garrett & Dunner L.L.P.

(57) ABSTRACT

The present application relates to a novel family of double para-phenylenediamines joined by a linker arm substituted with one or more carboxylic radicals and/or derivatives and to the use thereof for the dyeing of keratin fibres.

These novel para-phenylenediamines are useful as oxidation bases for the dyeing of keratin fibres.

24 Claims, No Drawings

OTHER PUBLICATIONS

Co-pending U.S. Appl. No. 11/476,816, Title: Novel Double Para-Ohenylendeiamines Joined By A Linkage Comprising A Saturated Cyclic Radical And Use In Dyeing Inventors: Stéphane Sabelle et al. U.S. Filing Date: Jun. 29, 2006.

Co-pending U.S. Appl. No. 11/476,815, Title: Double Para-Phenylendeiamines Joined By An Aromatic Group And Process For Dyeing eratin Fibers Inventors: Stéphane Sabelle et al. U.S. AFiling Date: Jun. 29, 2006.

Co-pending U.S. Appl. No. 11/476,823, Title: Novel Double Para-Phenylenediamines Joined By A Branched Aliphatic Group And Method Of Dyeing Keratin Fibers Inventors: Stéphane Sabelle et al. U.S. Filing Date: Jun. 29, 2006.

Co-pending U.S. Appl. No. 11/476,824, Title: Novel Double Para-Phenylenediamines Joined By A Linkage Comprising An Atom Chosen From Sulphur And Nitrogen And Method For Dyeing Keratinous Fibers Inventors: Stéphane Sabelle et al. U.S. Filin Date: Jun. 29, 2006.

Co-pending U.S. Appl. No. 11/476,822, Title: Novel Double Para-Phenylenediamines Joined By A Linker Arm Substituted With At Least One Group Chosen From Hydroxyl, Alkoxy, And/Or Amino Groups And Method Of Dyeing Keratinous Fibers Inventors: Stéphane Sabelle et al. U.S. Filing Date: Jun. 29, 2006.

Office Action in co-pending U.S. Appl. No. 11/476,816 dated Mar. 4, 2008, Ex. Eisa Elhilo.

Office Action in co-pending U.S. Appl. No. 11/476,823 dated Mar. 4, 2008, Ex. Eisa Elhilo.

Office Action in co-pending U.S. Appl. No. 11/476,824 dated Mar. 6, 2008, Ex. Eisa Elhilo.

International Search Report for EP 06 11 6056, dated Jul. 10, 2006 (corresponding to U.S. Appl. No. 11/476,816).

International Search Report for EP 06 11 6073, dated Aug. 30, 2006 (corresponding to U.S. Appl. No. 11/476,815).

International Search Report for EP 06 11 6072, dated Nov. 13, 2006 (corresponding to U.S. Appl. No. 11/476,823).

International Search Report for EP 06 11 6070, dated Nov. 14, 2006 (corresponding to U.S. Appl. No. 11/476,824).

International Search Report for EP 06 11 6068, dated Nov. 13, 2006 (corresponding to U.S. Appl. No. 11/476,822).

International Search Report for EP 06 11 6066, dated Oct. 31, 2006 (corresponding to the present application).

International Search Report for FR 0551805, dated Feb. 14, 2006 (corresponding to U.S. Appl. No. 11/476,816).

International Search Report for FR 0551806, dated Feb. 1, 2006 (corresponding to U.S. Appl. No. 11/476,815).

International Search Report for FR 0551807, dated May 5, 2006 (corresponding to U.S. Appl. No. 11/476,823).

International Search Report for FR 0551808, dated May 5, 2006 (corresponding to U.S. Appl. No. 11/476,824).

International Search Report for FR 0551809, dated May 5, 2006 (corresponding to U.S. Appl. No. 11/476,822).

International Search Report for FR 0551810, dated May 4, 2006 (corresponding to the present application).

English Language DERWENT Abstract for EP 0 770 375 (1007).

English Language DERWENT Abstract for JP 2-019576 (1990).

English Language DERWENT Abstract for JP 5-163124 (1993).

English Language DERWENT Abstract for JP 8-041329 (1996).

Giastas et al., "Pseudorotaxanes of β-cyclodextrin with diamino end-functionalized oligo-phenyl and -benzyl compunds in solution and in the solid state," *Journal of Inclusion Phenomena and Marcorcyclic Chemistry*, 44: 247-250 (2002).

Kolsaker et al., "Ozonation of p-nitro-N,N-dimethylaniline," *Advances in Chemsitry Series: Ozone Reaction with Organic Compounds*, 112: 101-113 (1972).

Kotsuki et al., "High pressure organic chemistry; XII. A convenient synthesis of aromatic amines from activated aromatic fluorides," *Synthesis*, 12:1147-1148 (1990).

Massa et al., "Spiro-[4-H-pyrrolo[1,2-a][1,4]benzodiazepine-4,4'-piperdine] derivatives as potential nootropic agents: a simple one-pot synthesis," *Synth. Comm.*, 20(22):3537-3545 (1990).

Mikuriya et al., "Binuclkear nickel(II) complexes of Schiff bases derived from salicylaldehydes and 1,n-diamino-n'-hydroxyalkanes (n,n' = 3,2;4,2; and 5,3) having an endogenous alkoxo bridge and a pyrazolato exogenoous bridge," *Bull. Chem. Soc. Jpn.*, 65(2) :334-339 (1992).

Mikuriya et al., Alkoxo-bridges dinuclear and tetranuclear copper(II) complexes with Schiff bases derived from benzoylacetone and 1,n-diamino-n'-hydroxyalkanes (n.n' = 3,2; 4,2; and 5,3) *Bull. Chem. Soc. Jpn.*, 75:2595-2607 (2002).

Murase et al., "Synthesis and characterization of cooper(II) and nikel(H) complexes of 1,5-diamino-3-pentanol and its derivatives," *Bull. Chem. Soc. Jpn.*, 55:2404-2408 (1982).

Nalwa et al., "Aromatic polyureas: a new class of nonlinear optical polymer with large second-harmonic generation," *Electronics Letters*, 28(15): 1409-1411 (1992).

Nir & Seligman "Ultrastructural localization of oxidase activities in corn root tip cells with two new osmiophilic reagents compared to diaminobenzidine," *Journal of Histochemistry and Cytochemsitry*, 19(10): 611-620 (1971).

Pienaar et al., "1-oxo-2,8-diaryl-2,5,8-triaza-1λ-5-phosphabicylo[3.3.0]octanes as substrates for the preparation of bis(2-arylaminoethyl)amines," *Synthesis*, 9: 1315-1319 (2000).

Seligman et al., "Some cytochemical correlations between oxidase activity (cytochrome and peroxidase) and chemical structure of bis(phenylenediamines)," *Histochemie*, 22: 85-89 (1970).

Sherer et al., "Synthesis and exploratory photophysical investigation of donor-bridge-acceptor systems derived from N-substituted 4-piperidones," *Recueil des Travaux Chimiques des Pays-Bas*, 112:535-548 (1993).

Winkelmann et al., "Chemotherapeutically active nitro compounds. 1. Nitroanilines," *Arzneimittel-Forschung*, 25(5): 681-708 (1975).

CAS Abstract No. XP001094496: Chen et al., "Chemical behavior of N-aryl nitrogenoxosquaric acid in alcohols," *Sichuan Daxue Xueba, Ziran Kexue - Acta Scietiarum Naturalium Universitatis Szechuanensis, SSU Ch'Uan Ta Hsueh, Cheng-Tu,* 35(1); 141-143 (1998).

CAS Abstract No. XP002405185 for EP 1 739 084 (2007).

* cited by examiner

DOUBLE PARA-PHENYLENEDIAMINES JOINED BY A LINKER ARM SUBSTITUTED WITH ONE OR MORE CARBOXYLIC RADICALS AND/OR DERIVATIVES AND USE IN DYEING

CROSS-REFERENCES TO RELATED APPLICATION

This application claims benefit of U.S. Provisional Application No. 60/698,936, filed Jul. 14, 2005, the contents of which are incorporated herein by reference. This application also claims benefit of priority under 35 U.S.C. § 119 to French Patent Application No. FR 05 51810, filed Jun. 29, 2005, the contents of which are also incorporated herein by reference.

FIELD OF THE INVENTION

The present application relates to a novel family of double para-phenylenediamines joined by a linker arm substituted with one or more carboxylic radicals and/or derivatives and to the use thereof for the dyeing of keratin fibres.

BACKGROUND OF THE INVENTION

The dyeing of keratin fibres, and in particular human hair, with dye compositions containing oxidation dye precursors, generally called oxidation bases, such as ortho- or para-phenylenediamines, ortho- or para-aminophenols and heterocyclic compounds, is known. These oxidation bases are colourless or weakly coloured compounds which, when combined with oxidizing products, can give rise, by a process of oxidative condensation, to coloured compounds.

It is also known that it is possible to vary the shades obtained with these oxidation bases by combining them with couplers or dyeing modifiers, the latter being chosen in particular from aromatic meta-diaminobenzenes, meta-aminophenols, meta-diphenols and certain heterocyclic compounds, such as indole compounds and pyridine compounds.

The variety of molecules used in terms of oxidation bases and couplers makes it possible to obtain a rich palette of colours.

The "permanent" dyeing obtained using these oxidation dyes must, moreover, satisfy a certain number of requirements. Thus, it must not present any problem of a toxicological nature, it must make it possible to obtain shades of the desired intensity and must have good resistance to external agents such as light, bad weather, washing, permanent waving, perspiration and rubbing.

The dyes must also provide coverage of white hair, and finally must display minimum selectivity, i.e. ensure that the smallest possible differences in coloration are obtained all the way along the same keratin fibre, which generally is differently sensitized (i.e. damaged) between its tip and its root.

SUMMARY OF THE INVENTION

The aim of the present invention is to provide novel oxidation bases capable of dyeing keratin fibres in a variety of strong, aesthetic shades with low selectivity, and also colours that are resistant to the various aggressive factors to which the fibres may be subjected, such as light, sweat and shampoos.

DETAILED DESCRIPTION OF THE INVENTION

This aim is achieved with the present invention, a subject of which is a novel family of double para-phenylenediamines of the following formula (I) and also the corresponding addition salts:

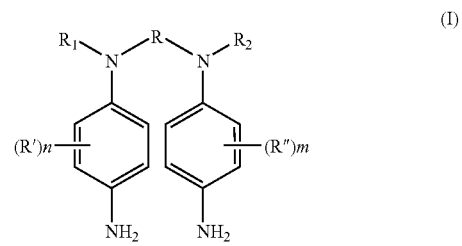

in which:

R represents a linear or branched $C_1$-$C_{10}$ alkylene radical substituted with one or more radicals:

carboxyl aminocarbonyl (($C_1$-$C_6$)monoalkyl or ($C_1$-$C_6$)dialkyl)aminocarbonyl ($C_1$-$C_{16}$)alkoxycarbonyl, $R_1$ and $R_2$ represent, independently of one another, a hydrogen atom a linear or branched $C_1$-$C_6$ alkyl radical a linear or branched $C_1$-$C_6$ alkyl radical substituted with one or more hydroxyl, $C_1$-$C_4$ alkoxy, amino, ($C_1$-$C_4$) monoalkylamino or ($C_1$-$C_4$)dialkylamino radicals, R' and R" represent, independently of one another, a $C_1$-$C_6$ alkyl radical a $C_1$-$C_6$ alkoxy radical a hydroxy($C_1$-$C_6$)alkoxy radical a ($C_1$-$C_6$)alkoxy($C_1$-$C_6$)alkyl radical a mono- or polyhydroxy($C_1$-$C_6$)alkyl radical, n and m represent, independently of one another, an integer between 0 and 4, apart from

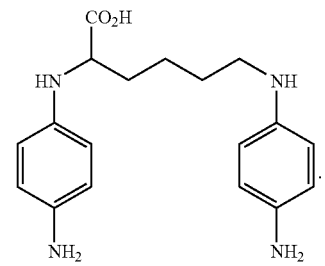

The composition of the present invention makes it possible in particular to obtain a very strong coloration of keratin fibres, of low selectivity, and resistant, in particular to light.

Another subject of the invention relates to compositions for the dyeing of keratin fibres, in particular human keratin fibres, such as the hair, containing at least one para-phenylenediamine of formula (I).

A subject of the invention is also a method of dyeing employing this composition, the use of the composition according to the present invention for the dyeing of keratin fibres, in particular human keratin fibres, such as the hair, and a device with several compartments or dyeing "kit".

The following para-phenylenediamines may be mentioned as examples:

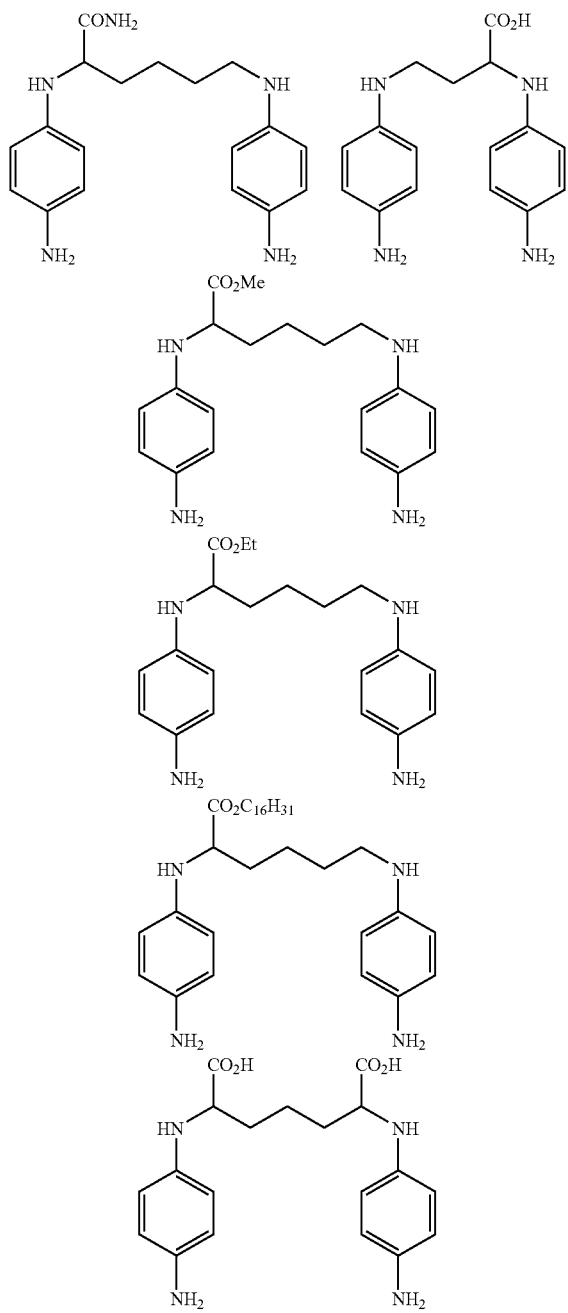

According to a particular embodiment, the para-phenylenediamines of formula (I) are such that $R_1$ and $R_2$ represent independently a hydrogen atom or a $C_1$-$C_4$ alkyl group that can be substituted. R preferably represents a linear or branched $C_2$-$C_7$ alkylene radical substituted with one or more ($C_1$-$C_4$)alkoxycarbonyl, carboxyl or aminocarbonyl radicals. According to a particular embodiment, n and m are equal to 0 or 1.

In general, the addition salts that can be used are in particular chosen from the addition salts with an acid, such as hydrochloric acid, hydrobromic acid, sulphuric acid, citric acid, succinic acid, tartaric acid, lactic acid, para-toluenesulphonic acid, benzenesulphonic acid, phosphoric acid and acetic acid.

They can also be in the form of solvates, for example a hydrate or a solvate of a linear or branched alcohol such as ethanol or isopropanol.

The para-phenylenediamines of formula (I) according to the present application can be prepared according to a conventional method of synthesis. Reference may be made, for example, to patent application DE10144226A.

By way of illustration, the para-phenylenediamines of formula (I) can be synthesized according to the following reaction scheme:

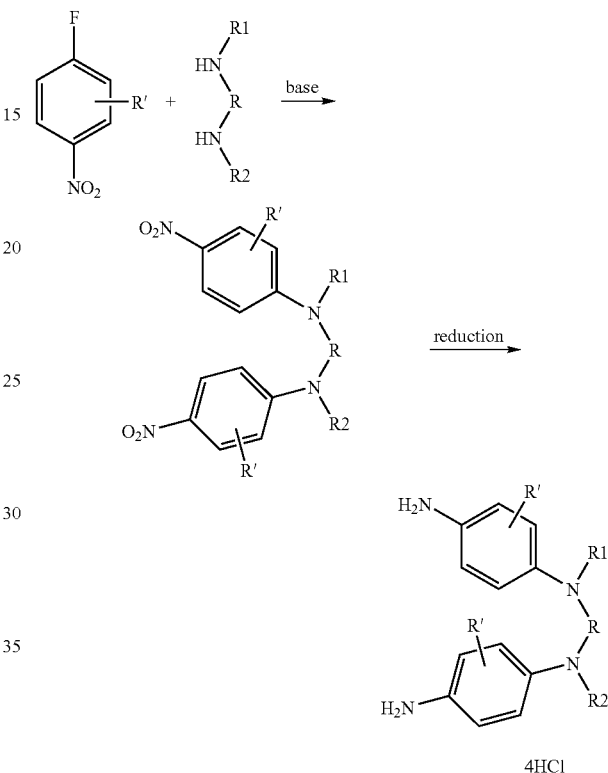

The first stage in the synthesis is a nucleophilic substitution of a diamine on a derivative of para-fluoronitrobenzene, a stage suggested by the publications Synthesis 1990 (12), 1147-1148 and Synth. Commun. 1990, 20 (22), 3537-3545. The second stage is a conventional reduction stage, and can for example be a reaction of hydrogenation by heterogeneous catalysis in the presence of Pd/C, Pd(II)/C or Raney Ni, or else a reaction of reduction by a metal, for example by zinc, iron, tin, etc. (Advanced Organic Chemistry, 4th edition, 1992, J. March, Wiley Interscience; Reduction in Organic Chemistry, M. Hudlicky, 1983, Ellis Honwood series Chemical Science).

The present application also relates to the nitrogen-containing compounds of the following formula (II) which can be used for obtaining para-phenylenediamines of formula (I):

(II)

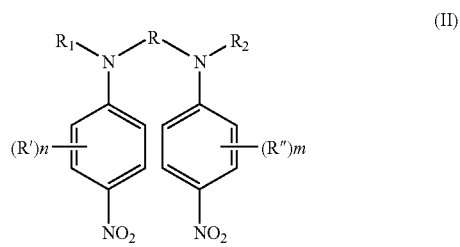

in which $R_1$, $R_2$, R', R", R, n and m are as defined above.

A subject of the invention is also a dyeing composition comprising, in a medium that is suitable for dyeing, at least one oxidation base of the type para-phenylenediamine of formula (I) as defined above.

The amount of para-phenylenediamine of formula (I) in the dye composition is generally between 0.0001 wt % and 20 wt % relative to the total weight of the composition, preferably between 0.01% and 10%.

The composition according to the invention preferably contains at least one oxidation coupler.

Among the oxidation couplers, mention may in particular be made of meta-phenylenediamines, meta-aminophenols, meta-diphenols, naphthalenic couplers and heterocyclic couplers and also their addition salts.

As examples, mention may be made of 2-methyl-5-aminophenol, 5-N-(β-hydroxyethyl) amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino) toluene, and their addition salts.

Generally, the amount of the oxidation coupler(s) is between 0.0001 and 20 wt %, preferably between 0.005 and 6 wt %, relative to the total weight of the composition.

The composition according to the invention can also contain at least one additional oxidation base different from the oxidation bases of formula (I).

The oxidation bases can in particular be selected from para-phenylenediamines, bisphenylalkylenediamines, para-aminophenols, ortho-aminophenols and heterocyclic bases, and their addition salts.

Among the para-phenylenediamines, mention may more particularly be made, by way of example, of: para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxy-ethyl) amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-thienyl-para-phenylenediamine, 2-βhydroxyethylamino-5-aminotoluene, 3-hydroxy-1(4'-aminophenyl)pyrrolidine, 6-(4-aminophenylamino)hexan-1-ol, and their addition salts with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, 6-(4-aminophenylamino)hexan-1-ol, and their addition salts with an acid are particularly preferred.

Among the bisphenylalkylenediamines, mention may be made, by way of example, of: N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4'-aminophenyl)tetramethylenediamine, N,N'-bis(β-hydroxyethyl)-N,N'-bis(4'-aminophenyl)tetramethylenediamine, N,N'-bis(4'-amino-3'-methylphenyl)-tetramethylenediamine, N,N'-bis(ethyl)-N,N'-bis(4'-amino-3'-methylphenyl)ethylenediamine, 1,8-bis(2,5-diaminophenxoy)-3,6-dioxaoctane, and their addition salts with an acid.

Among the para-aminophenols, mention may be made, for example, of: para-aminophenol, 4-amino-3-methylphenol, 4-amino-3-fluorophenol, 4-amino-2-chlorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2,6-dichlorophenol, 4-amino-6-[((5'-amino-2'-hydroxy-3'-methyl)phenyl)methyl]-2-methylphenol, bis(5'-amino-2'-hydroxy)phenylmethane, and their addition salts with an acid.

Among the ortho-aminophenols, mention may be made, by way of example, of: 2-aminophenol, 2-amino-5-methylphenol, 2-amino-6-methylphenol, 5-acetamido-2-aminophenol, 5-[(2-hydroxyethyl)amino]-2-methylphenol, and their addition salts with an acid.

Among the heterocyclic bases, mention may be made, by way of example, of: pyridine derivatives, pyrimidine derivatives and pyrazole derivatives.

Among the pyridine derivatives, mention may be made of the compounds described for example in patents GB 1026978 and GB 1153196, such as 2,5-diaminopyridine, 2-(4-methoxyphenyl)amino-3-aminopyridine, 3,4-diaminopyridine, and their addition salts with an acid.

Other pyridine oxidation bases that are useful in the present invention are the 3-aminopyrazolo[1,5-a]pyridine oxidation bases or their addition salts described, for example, in patent application FR 2801308. By way of example, mention may be made of: pyrazolo[1,5-a]pyridin-3-ylamine; 2-acetylaminopyrazolo[1,5-a]pyridin-3-ylamine; 2-morpholin-4-ylpyrazolo[1,5-a]pyridin-3-ylamine; 3-amino-pyrazolo[1,5-a]pyridine-2-carboxylic acid; 2-methoxypyrazolo[1,5-a]pyridin-3-ylamino; (3-aminopyrazolo[1,5-a]pyridin-7-yl)methanol; 2-(3-aminopyrazolo[1,5-a]pyridin-5-yl)ethanol; 2-(3-aminopyrazolo[1,5-a]pyridin-7-yl)ethanol; (3-aminopyrazolo[1,5-a]pyridin-2-yl)methanol; 3,6-diamino-pyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyridin-3-ylamine; pyrazolo[1,5-a]pyridine-3,5-diamine; 5-morpholin-4-ylpyrazolo[1,5-a]pyridin-3-ylamine; 2-[(3-aminopyrazolo[1,5-a]pyridin-5-yl)-(2-hydroxyethyl)amino] ethanol; 2-[(3-aminopyrazolo[1,5-a]pyridin-7-yl)-(2-hydroxyethyl)amino]ethanol; 3-aminopyrazolo[1,5-a]pyridin-5-ol. 3-aminopyrazolo[1,5-a]pyridin-4-ol; 3-aminopyrazolo[1,5-a]pyridin-6-ol; 3-aminopyrazolo[1,5-a]pyridin-7-ol; and also their addition salts with an acid.

Among the pyrimidine derivatives, mention may be made of the compounds described for example in patents DE 2359399; JP 88-169571; JP 05-63124; EP 0770375 or patent application WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and their addition salts and their tautomeric forms, when a tautomeric equilibrium exists.

Among the pyrazole derivatives, mention may be made of the compounds described in patents DE 3843892 and DE 4133957 and patent applications WO 94/08969, WO 94/08970, FR-A-2733749 and DE 19543988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazino-pyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methyl-pyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylamino-pyrazole, 3,5-diamino-4-(β-hydroxyethyl)amino-1-methylpyrazole, and their addition salts.

Generally, the concentration of the additional oxidation base(s) is between 0.0001 and 20 wt %, preferably between 0.005 and 6 wt %, relative to the total weight of the composition.

The dyeing composition in accordance with the invention can also contain one or more direct dyes which can in particular be selected from the neutral, acid or cationic nitrogen-containing dyes of the benzene series, the neutral, acid or cationic direct azo dyes, the neutral, acid or cationic quinone and in particular anthraquinone direct dyes, the azine direct dyes, the methinine, azomethinine, triarylmethane and indoamine direct dyes and the natural direct dyes. Preferably, the composition according to the invention contains at least one dye selected from the cationic direct dyes and the natural direct dyes.

Among the cationic direct dyes that can used according to the invention, mention may be made of the cationic azo direct dyes described in patent applications WO 95/15144, WO 95/01772 and EP-714954.

Among these compounds, mention may most particularly be made of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulphate.

Among the natural direct dyes that can be used in accordance with the invention, mention may be made of: lawsone, juglone, alizarin, purpurin, carminic acid, kermesic acid, purpurogallin, protocatechaldehyde, indigo, isatin, curcumine, spinulosine and apigenidine. It is also possible to use extracts or decoctions containing these natural dyes, and in particular henna-based cataplasms or extracts.

The direct dye(s) preferably represent(s) about from 0.001 to 20 wt % of the total weight of the ready-to-use composition, and even more preferably about from 0.005 to 10 wt %.

The medium that is suitable for dyeing advantageously consists of water or of a mixture of water and of at least one organic solvent such as, for example, linear or branched $C_1$-$C_4$ lower alcohols, such as ethanol and isopropanol; polyols and polyol ethers such as 2-butoxyethanol, propylene glycol, propylene glycol monomethyl ether, diethylene glycol monoethyl ether and diethylene glycol monomethyl ether, glycerol, and also aromatic alcohols such as benzyl alcohol or phenoxyethanol, and mixtures thereof.

The solvents are preferably present in proportions preferably of between about 1 and 40 wt % relative to the total weight of the dyeing composition, and even more preferably of between about 5 and 30 wt %.

Advantageously, the dyeing composition contains at least one cosmetic adjuvant selected from antioxidants, penetrants, sequestering agents, perfumes, buffers, dispersants, surfactants, conditioners, film-forming agents, polymers, ceramides, preservatives, lustre agents or opacifiers, vitamins or provitamins.

The above adjuvants are generally present in an amount, for each of them, of between 0.01 and 20 wt % relative to the weight of the composition.

The pH of the composition in accordance with the invention is generally between about 3 and 12, and preferably between about 5 and 11. It can be adjusted to the desired value by means of acidifying or basifying agents normally used in the dyeing of keratin fibres or alternatively by means of conventional buffer systems.

Among the acidifying agents, mention may be made, by way of example, of: inorganic or organic acids other than dicarboxylic acids, such as hydrochloric acid, orthophosphoric acid or sulphuric acid, carboxylic acids, such as acetic acid, tartaric acid, citric acid or lactic acid, and sulphonic acids.

Among the basifying agents, mention may be made, by way of example, of: aqueous ammonia, alkali metal carbonates, alkanolamines such as mono-, di- and triethanolamines and also their derivatives, sodium hydroxide, potassium hydroxide, and the compounds of formula:

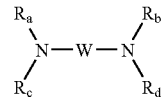

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom, a $C_1$-$C_4$ alkyl radical or a $C_1$-$C_4$ hydroxyalkyl radical.

Of course, a person skilled in the art will ensure that the adjuvant(s), additional oxidation dye precursor(s), oxidation coupler(s) and direct dye(s) are selected in such a way that the advantageous properties intrinsically associated with the oxidation dyeing composition in accordance with the invention are not, or not substantially, adversely affected by addition(s) that are envisaged.

The dyeing composition according to the invention can be in various forms, such as in the form of liquids, creams or gels, or any other form that is suitable for carrying out dyeing of keratin fibres, and in particular of human hair.

Another subject of the present application relates to a method for the dyeing of keratin fibres in which the composition of the invention as defined above is applied to the fibres, and the colour is developed by means of an oxidizing agent. The colour can be developed at acid, neutral or alkaline pH. The oxidizing agent can be added to the composition of the invention right at the moment of use. It can be used by means of an oxidizing composition containing it, applied simultaneously with or sequentially to the composition of the invention.

By way of oxidizing agents, mention may be made of hydrogen peroxide, urea peroxide, alkali metal bromates, per-salts such as perborates and persulphates, peracids and oxydase enzymes, among which mention may be made of peroxydases, 2-electron oxydoreductases such as uricases and 4-electron oxygenases such as laccases, hydrogen peroxide being particularly preferred.

According to a particular embodiment, the composition according to the present invention is mixed, preferably at the moment of use, with a composition containing, in a medium suitable for dyeing, at least one oxidizing agent, this oxidizing agent being present in a sufficient amount for developing a dye. The mixture obtained is then applied to the keratin fibres. After a holding time of about 3 to 50 minutes, preferably about 5 to 30 minutes, the keratin fibres are rinsed, washed with shampoo, rinsed again and then dried.

The oxidizing composition can contain various adjuvants used conventionally in compositions for hair dyeing and as defined above.

The pH of the oxidizing composition containing the oxidizing agent is such that, after mixing with the dyeing composition, the pH of the resulting composition applied to the keratin fibres preferably ranges between about 3 and 12, and even more preferably between 5 and 11. It can be adjusted to the desired value by means of acidifying or basifying agents normally used in the dyeing of keratin fibres and as defined above.

The ready-to-use composition which is finally applied to the keratin fibres can be in various forms, such as in the form of liquids, creams or gels or any other form suitable for carrying out dyeing of keratin fibres, especially human keratin fibres, and in particular human hair.

The present application also relates to the use of the cosmetic composition according to the invention containing, in a medium suitable for dyeing, at least one para-phenylenediamine of formula (I) for the dyeing of keratin fibres, preferably human keratin fibres such as the hair.

A subject of the invention is also a multicompartment device or dyeing "kit" in which a first compartment contains a dyeing composition containing a para-phenylenediamine of formula (I) and a second compartment contains an oxidizing composition. This device can be equipped with a means for delivering the desired mixture onto the hair, such as the devices described in patent FR-2 586 913 in the name of the applicant.

EXAMPLES OF SYNTHESIS

Example 1

Synthesis of ethyl-2,6-bis[(4-aminophenyl)amino]hexanoate tetrahydrochloride (3)

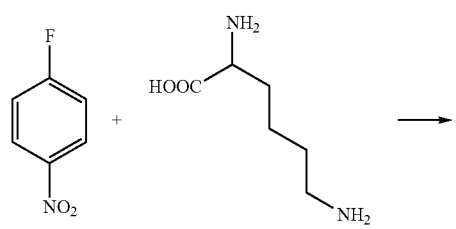

-continued

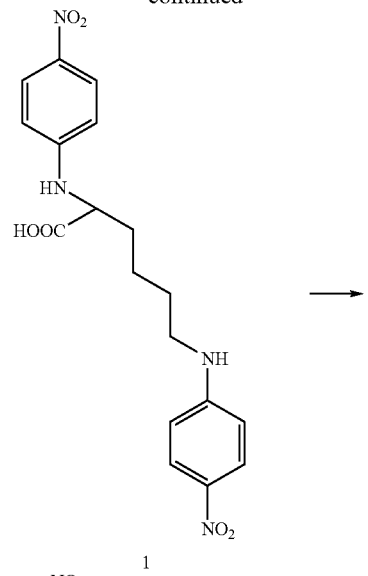

1

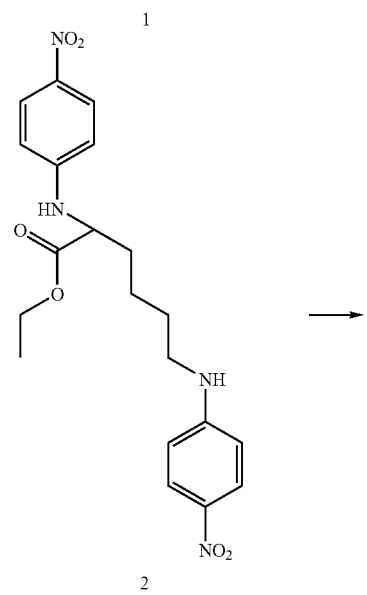

2

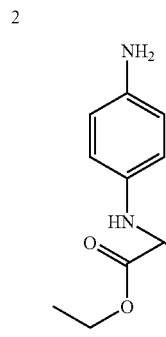

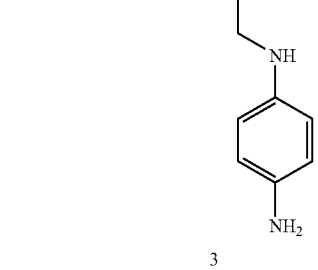

3

Stage 1: Synthesis of 2,6-bis[(4-nitrophenyl)amino]hexanoic acid (1)

5 g (34.2 mmol) of L-lysine are dissolved in 100 ml of water in the presence of 1.4 g (1 eq.) of sodium hydroxide and 8.6 g (3 eq.) of sodium bicarbonate, in a 250 ml three-necked flask equipped with a condenser and a thermometer. A solution of 10.8 ml (3 eq.) of 4-fluoronitrobenzene in 60 ml of ethanol is poured onto the mixture, which is brought to reflux (85°-90° C.) for 5 days. The cooled mixture is extracted with ethyl ether. The aqueous phase is acidified to pH ~3 with 5 N hydrochloric acid. A gum-like precipitate forms and is extracted with dichloromethane in the presence of a small amount of methanol. The organic phase is washed with water until neutrality is reached, dried over sodium sulphate, and then evaporated to give an orange-coloured oil which crystallizes in the presence of ethyl ether. 11.7 g of a yellow crystalline product are obtained, i.e. an 88% yield.

Stage 2: Synthesis of ethyl 2,6-bis[(4-nitrophenyl)amino]hexanoate (2)

5 g of 2,6-bis[(4-nitrophenyl)amino]hexanoic acid dissolved in 50 ml of ethanol and 1.5 ml of sulphuric acid are introduced into a 100 ml three-necked flask equipped with a condenser and a thermometer, and the mixture is then refluxed overnight.

The homogeneous mixture is subsequently cooled and then evaporated to dryness. The residue is taken up with dichloromethane and the resulting organic phase is then washed with a saturated aqueous 1 N sodium hydrogen carbonate solution, then with water.

After drying over sodium sulphate, the organic phase is evaporated to dryness. A yellow solid having a mass of 2.9 g is obtained, with a 54% yield.

Stage 3: Synthesis of ethyl 2,6-bis[(4-aminophenyl)amino]hexanoate tetrahydrochloride (5)

2 g of ethyl 2,6-bis[(4-nitrophenyl)amino]hexanoate dissolved in 100 ml of a mixture of isopropanol/water (7/3) are introduced into a 250 ml hydrogenator in the presence of 4 g of palladium-on-charcoal.

After the introduction of hydrogen for one hour at 53° C. and under 10 bar, the reaction medium is filtered and then concentrated under vacuum.

This medium is taken up with a mixture of isopropanol/acetone/HCl (4 N) and the precipitate obtained is then filtered and washed with ethyl ether. 1.8 g of ethyl 2,6-bis[(4-aminophenyl)amino]hexanoate tetrahydrochloride (5) are obtained, with a 75% yield.

The proton NMR and mass spectra are in accordance with the expected structure of the product.

Example 2

Synthesis of 2,6-bis[(4-aminophenyl)amino]heptanedioic acid tetrahydrochloride (5)

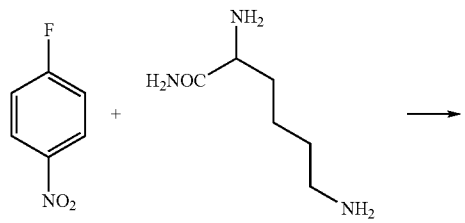

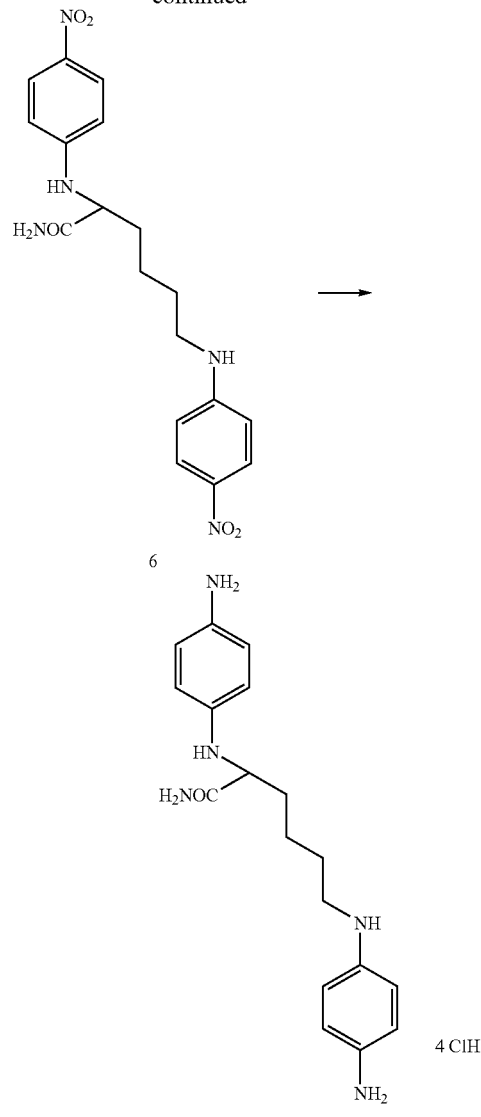

Stage 1: Synthesis of 2,6-bis[4-nitrophenyl)amino]heptanedioic acid (4)

5 g of 2,6-diaminopinelic acid dissolved in 50 ml of water, 2.1 g of sodium hydroxide (2 eq.) and 6.6 g of sodium hydrogen carbonate are introduced into a 250 ml three-necked flask. 8.4 ml of 4-fluoronitrobenzene in solution in 50 ml of ethanol are then poured into the mixture and the reaction is brought to reflux for 4 days. The mixture is then cooled, and the aqueous phase is acidified to pH=3 with 1 N HCl. An oily brown deposit forms; the reaction medium is extracted with dichloromethane and ethanol. Ethyl ether is then added in order to initiate crystallization. After filtration and drying of the solid formed, 7.7 g of an orange solid are obtained, with a 68% yield.

Stage 2: Synthesis of 2,6-bis[4-(aminophenyl)amino]heptanedioic acid tetrahydrochloride (5)

3 g of 2,6-bis[(4-nitrophenyl)amino]heptanedioic acid and 3 g of palladium-on-charcoal in a mixture of 70/30 ml ethanol/water are introduced into the 250 ml hydrogenator. The product is hydrogenated under 7 bar for 1 hour at ambient temperature. Under nitrogen, the mixture is withdrawn and recovered in 50 ml of water and 5.5 ml of 5 N HCl; the mixture is filtered over celite and then washed with water.

The filtrate is evaporated to dryness and then taken up in acetone. The solid is then filtered off and washed with acetone then with ethyl ether.

After drying, 2.4 g of a cream solid are obtained, with a 67% yield.

The proton NMR and mass spectra are in accordance with the expected structure of the product.

Example 3

Synthesis of 2,6-bis[(4-aminophenyl)amino]hexanamide tetrahydrochloride (7)

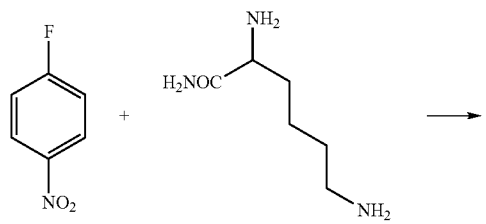

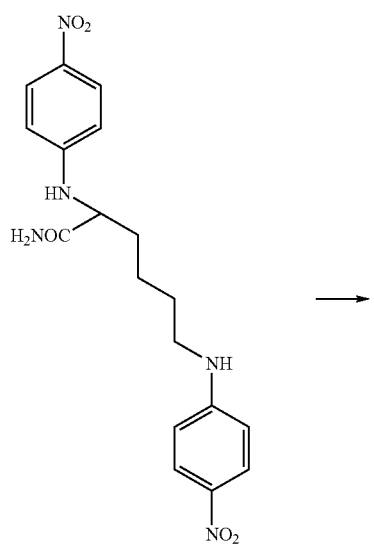

6

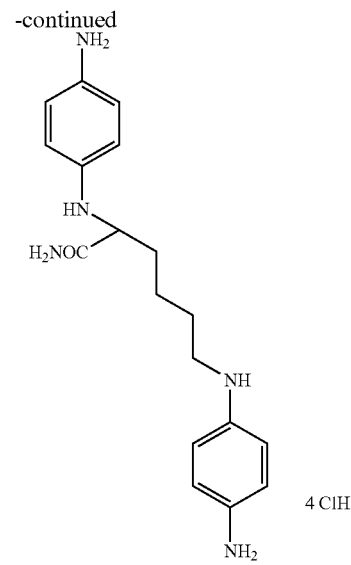

5

Stage 1: Synthesis of 2,6-bis[(4-nitrophenyl)amino]heptanedioic acid (4)

2.3 g of 4-fluoronitrobenzene (2 eq.) are dissolved in 10 ml of DMSO. 1.2 equivalents of 2,6-diaminohexanamide and 4 equivalents of triethylamine are added to the solution. The reaction medium is brought to 60° C. for 24 hours. The mixture is then poured over crushed ice, and a precipitate forms. The latter is filtered off, washed with water, and then dried.

Stage 2: Synthesis of 2,6-bis[(4-amino-phenyl)amino]hexanamide tetrahydrochloride (5)

0.815 mg of 2,6-bis[(4-nitrophenyl)amino]heptanedioic acid (4) and 140 mg of palladium-on-charcoal in 100 ml of ethanol are introduced into a 250 ml hydrogenator. The product is hydrogenated under 7 bar for 1 hour at ambient temperature. Under nitrogen, the mixture is withdrawn and recovered in 50 ml of isopropanol and 5.5 ml of hydrochloric isopropanol. After the addition of isopropyl ether to the filtrate, the solid is filtered off over celite and then washed with acetone and with ethyl ether.

After drying, 755 mg of a cream solid are obtained.

The proton NMR and mass spectra are in accordance with the expected structure of the product.

Examples of Dyeing

Examples 1 to 14

Dyeing Composition Based on 2,6-bis[(4-amino-phenyl)amino]hexanamide tetrahydrochloride (7)

Examples 1 to 7

Dyeing in an Acid Medium

The following dyeing compositions are prepared:

|  | Example | | | | | | |
|---|---|---|---|---|---|---|---|
|  | 1 | 2 | 3 | 4 | 5 | 6 | 7 |
| 2,6-bis[(4-Amino-phenyl)amino]hexanamide tetrahydrochloride (7) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methyl-phenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c]-[1,2,4]triazole | | | | | $10^{-3}$ mol | | |
| 2-(2,4-Diamino-phenoxy)ethanol hydrochloride | | | | | | $10^{-3}$ mol | |
| 3-Amino-2-chloro-6-methylphenol hydrochloride | | | | | | | $10^{-3}$ mol |
| Dye support (2) | (*) | (*) | (*) | (*) | (*) | (*) | (*) |
| Demineralized water q.s. | 100 g | 100 g | 100 g | 100 g | 100 g | 100 g | 100 g |
| 96° Ethyl alcohol | 20.8 g | | | | | | |
| Sodium metabisulphite, 35% aqueous solution | 0.23 g A.M | | | | | | |
| Pentasodium salt of diethylenetriaminepentaacetic acid, 40% aqueous solution | 0.48 g A.M | | | | | | |
| $C_8$-$C_{10}$ Alkyl polyglucoside, 60% aqueous solution | 3.6 g A.M | | | | | | |
| Benzyl alcohol | 2.0 g | | | | | | |
| Polyethylene glycol with 8 ethylene oxide units | 3.0 g | | | | | | |
| $Na_2HPO_4$ | 0.28 g | | | | | | |
| $KH_2PO_4$ | 0.46 g | | | | | | |

(*): Dye support (1) pH 7

At the moment of use, each composition is mixed with an equal weight of aqueous hydrogen peroxide at 20 volumes (6 wt %). A final pH of 7 is obtained.

Each mixture obtained is applied to locks of grey hair comprising 90% white hairs. After a holding time of 30 minutes, the locks are rinsed, washed with a standard shampoo, rinsed again and then dried.

The shades obtained are shown in the table below:

|  | Example | | | | | | |
|---|---|---|---|---|---|---|---|
|  | 1 | 2 | 3 | 4 | 5 | 6 | 7 |
| Shade observed | deep grey | deep grey-violet | deep grey-violet | deep red-brown | deep grey-violet-red | deep blue | deep violet |

Examples 8 to 14

Dyeing in a Basic Medium

The following dyeing compositions are prepared:

|  | Example | | | | | | |
|---|---|---|---|---|---|---|---|
|  | 8 | 9 | 10 | 11 | 12 | 13 | 14 |
| 2,6-bis[(4-Amino-phenyl)amino]hexanamide tetrahydrochloride (7) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methyl-phenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c]-[1,2,4]triazole | | | | | $10^{-3}$ mol | | |
| 2-(2,4-Diamino-phenoxy)ethanol hydrochloride | | | | | | $10^{-3}$ mol | |
| 3-Amino-2-chloro-6-methylphenol hydrochloride | | | | | | | $10^{-3}$ mol |

-continued

| Dye support (1) Demineralized water q.s. | (*) 100 g | (*) 100 g | (*) 100 g | (*) 100 g | (*) 100 g | (*) 100 g | (*) 100 g |
|---|---|---|---|---|---|---|---|
| 96° Ethyl alcohol | | | | 20.8 g | | | |
| Sodium metabisulphite, 35% aqueous solution | | | | 0.23 g A.M | | | |
| Pentasodium salt of diethylenetriaminepentaacetic acid, 40% aqueous solution | | | | 0.48 g A.M | | | |
| $C_8$-$C_{10}$ Alkyl polyglucoside, 60% aqueous solution | | | | 3.6 g A.M | | | |
| Benzyl alcohol | | | | 2.0 g | | | |
| Polyethylene glycol with 8 ethylene oxide units | | | | 3.0 g | | | |
| $NH_4Cl$ | | | | 4.32 g | | | |
| Aqueous ammonia containing 20% of $NH_3$ | | | | 2.94 g | | | |

(*): Dye support (2) pH 9.5

At the moment of use, each composition is mixed with an equal weight of aqueous hydrogen peroxide at 20 volumes (6 wt %). A final pH of 9.5 is obtained.

Each mixture obtained is applied to locks of grey hair comprising 90% of white hairs. After a holding time of 30 minutes, the locks are rinsed, washed with a standard shampoo, rinsed again and then dried.

The shades obtained are shown in the table below:

| Example | | | | | | | |
|---|---|---|---|---|---|---|---|
| | 8 | 9 | 10 | 11 | 12 | 13 | 14 |
| Shade observed | orangey brown | deep violet-red | red | red-brown | deep chromatic red | deep blue | deep violet |

What is claimed is:

1. A compound chosen from para-phenylenediamines of formula (I) and corresponding addition salts:

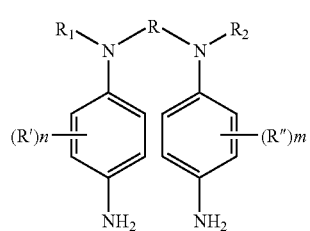

wherein:
R is chosen from linear or branched $C_1$-$C_{10}$ alkylene radicals substituted with at least one radical chosen from:
  carboxyl radicals,
  aminocarbonyl radicals,
  $(C_1$-$C_6)$monoalkyl amino carbonyl radicals,
  $(C_1$-$C_6)$dialkyl aminocarbonyl radicals, and
  $(C_1$-$C_{16})$alkoxycarbonyl radicals,
$R_1$ and $R_2$ which may be identical or different, are chosen from
  hydrogen,
  linear or branched $C_1$-$C_6$ alkyl radicals, and
  linear or branched $C_1$-$C_6$ alkyl radicals substituted with at least one radical chosen from hydroxyl, $C_1$-$C_4$ alkoxy, amino, $(C_1$-$C_4)$ monoalkylamino, and $(C_1$-$C_4)$dialkylamino radicals,
R' and R'', which may be identical or different, are chosen from
  $C_1$-$C_6$ alkyl radicals,
  $C_1$-$C_6$ alkoxy radicals,
  hydroxy$(C_1$-$C_6)$alkoxy radicals,
  $(C_1$-$C_6)$alkoxy$(C_1$-$C_6)$alkyl radicals,
  monohydroxy$(C_1$-$C_6)$alkyl radicals, and
  polyhydroxy$(C_1$-$C_6)$alkyl radicals, and
n and m, which may be identical or different, are each integers ranging from 0 to 4,
with the proviso that the compound is not a compound of formula (a):

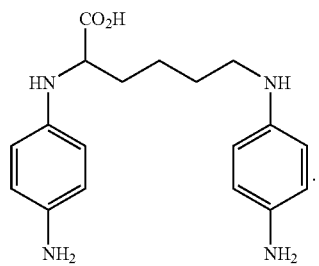

2. The compound of claim 1, in which R is chosen from linear or branched $C_2$-$C_7$ alkylene radicals substituted with at least one radical chosen from $(C_1$-$C_4)$alkoxycarbonyl, carboxyl, and aminocarbonyl radicals.

3. The compound of claim 1, in which $R_1$ and $R_2$, which may be identical or different, are chosen from hydrogen and optionally substituted $C_1$-$C_4$ alkyl groups.

4. The compound of claim 1, in which n and m are each, independently, 0 or 1.

5. The compound of claim 1, wherein the addition salts are acid addition salts chosen from hydrochloric acid, hydrobromic acid, sulphuric acid, citric acid, succinic acid, tartaric acid, lactic acid, para-toluenesuiphonic acid, benzenesulphonic acid, phosphoric acid, and acetic acid, wherein the addition salts may be optionally in the form of solvates.

6. The compound of claim 1, chosen from:

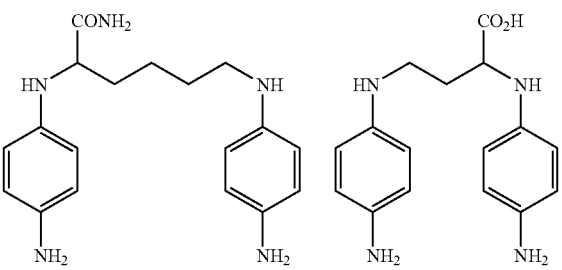

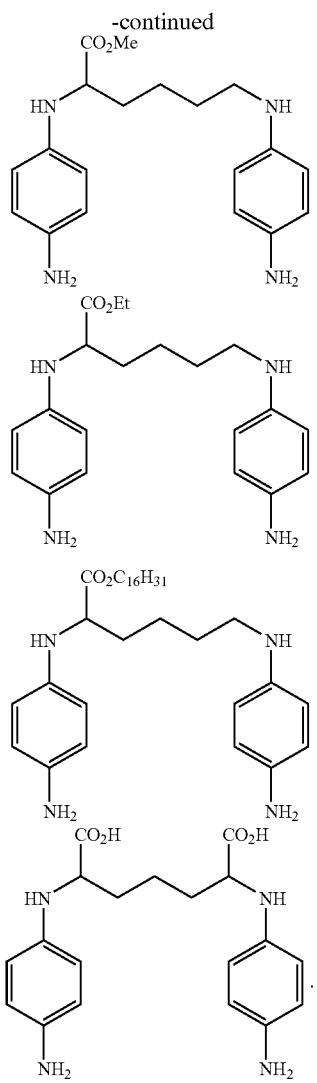

7. The compound of claim 6, chosen from:

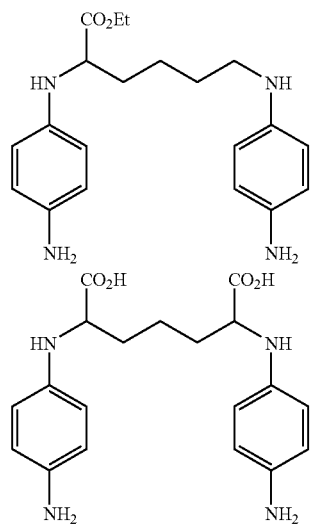

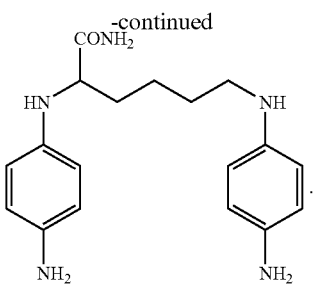

8. A dyeing composition comprising, in a medium that is suitable for dyeing, at least one oxidation base chosen from para-phenylenediamines of formula (I) and corresponding addition salts:

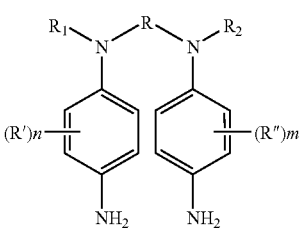

wherein:
R is chosen from linear or branched $C_1$-$C_{10}$ alkylene radicals substituted with at least one radical chosen from:
  carboxyl radicals,
  aminocarbonyl radicals,
  ($C_1$-$C_6$)monoalkyl amino carbonyl radicals,
  ($C_1$-$C_6$)dialkyl aminocarbonyl radicals, and
  ($C_1$-$C_{16}$)alkoxycarbonyl radicals,
$R_1$ and $R_2$, which may be identical or different, are chosen from
  hydrogen,
  linear or branched $C_1$-$C_6$ alkyl radicals, and
  linear or branched $C_1$-$C_6$ alkyl radicals substituted with at least one radical chosen from hydroxyl, $C_1$-$C_4$ alkoxy, amino, ($C_1$-$C_4$) monoalkylamino, and ($C_1$-$C_4$)dialkylamino radicals,
R' and R", which may be identical or different, are chosen from
  $C_1$-$C_6$ alkyl radicals,
  $C_1$-$C_6$ alkoxy radicals,
  hydroxy($C_1$-$C_6$)alkoxy radicals,
  ($C_1$-$C_6$)alkoxy($C_1$-$C_6$)alkyl radicals,
  monohydroxy($C_1$-$C_6$)alkyl radicals, and
  polyhydroxy($C_1$-$C_6$)alkyl radicals, and
n and m, which may be identical or different, are each integers ranging from 0 to 4,
with the proviso that the oxidation base is not a compound of formula (a):

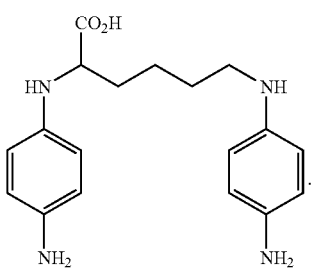

(a)

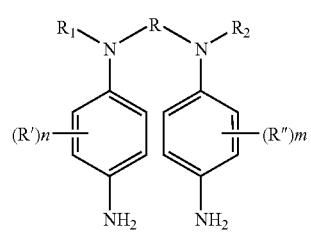

(I)

wherein:

R is chosen from linear or branched $C_1$-$C_{10}$ alkylene radicals substituted with at least one radical chosen from:
carboxyl radicals,
aminocarbonyl radicals,
(($C_1$-$C_6$)monoalkyl) amino carbonyl radicals,
(($C_1$-$C_6$)dialkyl) aminocarbonyl radicals, and
($C_1$-$C_{16}$)alkoxycarbonyl radicals, $R_1$ and $R_2$, which may be identical or different, are chosen from
hydrogen,
linear or branched $C_1$-$C_6$ alkyl radicals, and
linear or branched $C_1$-$C_6$ alkyl radicals substituted with at least one radical chosen from hydroxyl, $C_1$-$C_4$ alkoxy, amino, ($C_1$-$C_4$) monoalkylamino, and ($C_1$-$C_4$)dialkylamino radicals, R' and R", which may be identical or different, are chosen from
$C_1$-$C_6$ alkyl radicals,
$C_1$-$C_6$ alkoxy radicals,
hydroxy($C_1$-$C_6$)alkoxy radicals,
($C_1$-$C_6$)alkoxy($C_1$-$C_6$)alkyl radicals,
monohydroxy($C_1$-$C_6$)alkyl radicals, and
polyhydroxy($C_1$-$C_6$)alkyl radicals, and n and m, which may be identical or different, are each an integer ranging from 0 to 4, with the proviso that the oxidation base is not a compound of formula (a):

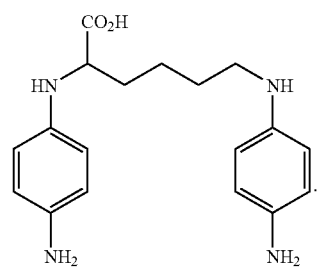

(a)

22. A multicompartment device comprising a first compartment containing at least one dyeing composition for dyeing keratin fibers and a second compartment containing at least one oxidizing agent, wherein the at least one dyeing composition comprises, in a medium that is suitable for dyeing, at least one oxidation base chosen from para-phenylenediamines of formula (I) and corresponding addition salts:

9. The composition of claim 8, wherein the at least one oxidation base is present in an amount ranging from 0.0001% to 20% by weight relative to the total weight of the composition.

10. The composition of claim 9, wherein the at least one oxidation base is present in an amount ranging from 0.01% to 10% by weight relative to the total weight of the composition.

11. The composition of claim 8, further comprising at least one oxidation coupler.

12. The composition of claim 11, wherein the at least one oxidation coupler is chosen from meta-phenylenediamines, meta-aminophenols, meta-diphenols, naphthalenic couplers, heterocyclic couplers, and addition salts thereof.

13. The composition of claim 8, further comprising at least one additional oxidation base different from the oxidation bases of formula (I).

14. The composition of claim 13, wherein the at least one additional oxidation base is chosen from para-phenylenediamines, bisphenylalkylenediamines, para-aminophenols, ortho-aminophenols, heterocyclic bases, and addition salts thereof.

15. The composition of claim 8, further comprising at least one direct dye.

16. The composition of claim 8, wherein the medium that is suitable for dyeing is chosen from water and mixtures of water and at least one organic solvent.

17. The composition of claim 16, wherein the at least one organic solvent is chosen from linear or branched $C_1$-$C_4$ lower alcohols, aromatic alcohols, and mixtures thereof.

18. The composition of claim 8, further comprising at least one cosmetic adjuvant chosen from antioxidants, penetrants, sequestering agents, perfumes, buffers, dispersants, surfactants, conditioners, film-forming agents, polymers, ceramides, preservatives, lustre agents, opacifiers, vitamins, and provitamins.

19. The composition of claim 18, wherein the at least one cosmetic adjuvant is present in the composition in an amount, for each of them, ranging from 0.01 to 20% by weight relative to the total weight of the composition.

20. The composition of claim 8, further comprising at least one oxidizing agent.

21. A method for dyeing keratin fibers, comprising applying at least one dyeing composition to the fibers in the presence of an oxidizing agent for a sufficient time for development of a desired coloration wherein the at least one dyeing composition comprises, in a medium that is suitable for dyeing, at least one oxidation base chosen from para-phenylenediamines of formula (I) and corresponding addition salts:

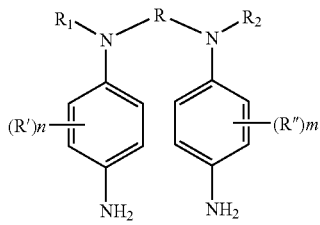

wherein:
R is chosen from linear or branched $C_1$-$C_{10}$ alkylene radicals substituted with at least one radical chosen from:
carboxyl radicals,
aminocarbonyl radicals,
(($C_1$-$C_6$)monoalkyl) aminocarbonyl radicals,
(($C_1$-$C_6$)dialkyl) aminocarbonyl radicals, and
($C_1$-$C_{16}$)alkoxycarbonyl radicals,
$R_1$ and $R_2$, which may be identical or different, are chosen from
hydrogen,
linear or branched $C_1$-$C_6$ alkyl radicals, and
linear or branched $C_1$-$C_6$ alkyl radicals substituted with at least one radical chosen from hydroxyl, $C_1$-$C_4$ alkoxy, amino, ($C_1$-$C_4$) monoalkylamino, and ($C_1$-$C_4$)dialkylamino radicals,
R' and R", which may be identical or different, are chosen from
$C_1$-$C_6$ alkyl radicals,
$C_1$-$C_6$ alkoxy radicals,
hydroxy($C_1$-$C_6$)alkoxy radicals,
($C_1$-$C_6$)alkoxy($C_1$-$C_6$)alkyl radicals,
monohydroxy($C_1$-$C_6$)alkyl radicals, and
polyhydroxy($C_1$-$C_6$)alkyl radicals, and
n and m, which may be identical or different, are each integers ranging from 0 to 4,
with the proviso that the oxidation base is not a compound of formula (a):

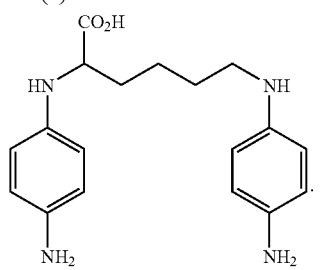

23. A method for the preparation of a compound chosen from para-phenylenediamines of formula (I) and corresponding addition salts:

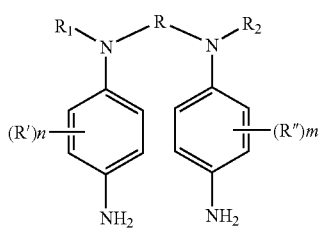

the method comprising reducing the nitrogen-containing compounds of formula (II):

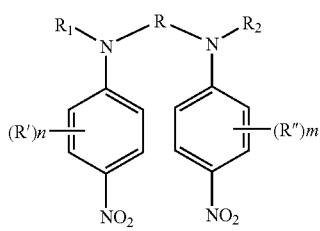

wherein:
R is chosen from linear or branched $C_1$-$C_{10}$ alkylene radicals substituted with at least one radical chosen from:
carboxyl radicals,
aminocarbonyl radicals,
(($C_1$-$C_6$)monoalkyl) amino carbonyl radicals,
(($C_1$-$C_6$)dialkyl) aminocarbonyl radicals, and
($C_1$-$C_{16}$)alkoxycarbonyl radicals,
$R_1$ and $R_2$, which may be identical or different, are chosen from
hydrogen,
linear or branched $C_1$-$C_6$ alkyl radicals, and
linear or branched $C_1$-$C_6$ alkyl radicals substituted with at least one radical chosen from hydroxyl, $C_1$-$C_4$ alkoxy, amino, ($C_1$-$C_4$) monoalkylamino, and ($C_1$-$C_4$)dialkylamino radicals,
R' and R", which may be identical or different, are chosen from
$C_1$-$C_6$ alkyl radicals,
$C_1$-$C_6$ alkoxy radicals,
hydroxy($C_1$-$C_6$)alkoxy radicals,
($C_1$-$C_6$)alkoxy($C_1$-$C_6$)alkyl radicals,
monohydroxy($C_1$-$C_6$)alkyl radicals, and
polyhydroxy($C_1$-$C_6$)alkyl radicals, and
n and m, which may be identical or different, are each integers ranging from 0 to 4,
with the proviso that the compound of formula (I) is not a compound of formula (a):

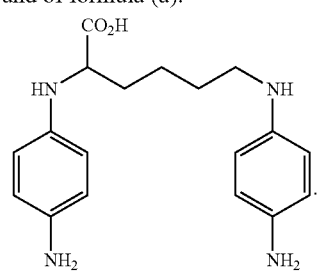

24. A nitrogen-containing compound of formula (II)

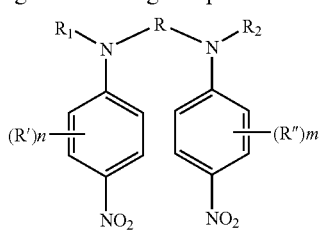

wherein:
R is chosen from linear or branched $C_1$-$C_{10}$ alkylene radicals substituted with at least one radical chosen from:
carboxyl radicals,
aminocarbonyl radicals,
(($C_1$-$C_6$)monoalkyl) amino carbonyl radicals,
(($C_1$-$C_6$)dialkyl) aminocarbonyl radicals, and
($C_1$-$C_{16}$)alkoxycarbonyl radicals, $R_1$ and $R_2$, which may be identical or different, are chosen from
hydrogen,
linear or branched $C_1$-$C_6$ alkyl radicals, and
linear or branched $C_1$-$C_6$ alkyl radicals substituted with at least one radical chosen from hydroxyl, $C_1$-$C_4$ alkoxy, amino, ($C_1$-$C_4$) monoalkylamino, and ($C_1$-$C_4$)dialkylamino radicals,
R' and R", which may be identical or different, are chosen from
$C_1$-$C_6$ alkyl radicals,
$C_1$-$C_6$ alkoxy radicals,
hydroxy($C_1$-$C_6$)alkoxy radicals,
($C_1$-$C_6$)alkoxy($C_1$-$C_6$)alkyl radicals,
monohydroxy($C_1$-$C_6$)alkyl radicals, and
polyhydroxy($C_1$-$C_6$)alkyl radicals, and
n and m, which may be identical or different, are each integers ranging from 0 to 4,
with the proviso that the nitrogen-containing compound is not:

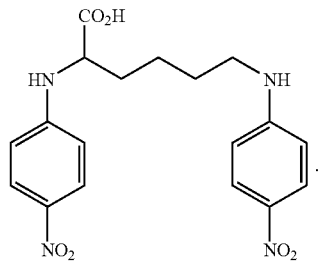

* * * * *

UNITED STATES PATENT AND TRADEMARK OFFICE
CERTIFICATE OF CORRECTION

| | |
|---|---|
| PATENT NO. | : 7,413,580 B2 |
| APPLICATION NO. | : 11/476821 |
| DATED | : August 19, 2008 |
| INVENTOR(S) | : Thierry Bordier and Stéphane Sabelle |

It is certified that error appears in the above-identified patent and that said Letters Patent is hereby corrected as shown below:

Claim 5, col. 18, line 51, delete "para-toluenesuiphonic" and insert --para-toluenesulphonic--.

Claim 23, col. 24, line 25, delete "$(C_1-C_4$" and insert --$(C_1-C_4)$--.

Signed and Sealed this

Twenty-first Day of October, 2008

JON W. DUDAS
*Director of the United States Patent and Trademark Office*